United States Patent [19]

Ohno et al.

[11] Patent Number: 5,675,046
[45] Date of Patent: Oct. 7, 1997

[54] PROCESS FOR PRODUCING PERFLUOROCARBON

[75] Inventors: Hiromoto Ohno; Tetsuo Nakajo; Tatsuharu Arai; Toshio Ohi, all of Kanagawa, Japan

[73] Assignee: Showa Denko K.K., Tokyo, Japan

[21] Appl. No.: 630,350

[22] Filed: Apr. 10, 1996

[51] Int. Cl.$^6$ .................................................. C07C 17/10
[52] U.S. Cl. .................................................. 570/134
[58] Field of Search .............................................. 570/134

[56] References Cited

U.S. PATENT DOCUMENTS

| 4,377,715 | 3/1983 | Nychka et al. | 570/123 |
| 4,929,317 | 5/1990 | Nishimura et al. | 204/59 R |

*Primary Examiner*—C. Warren Ivy
*Assistant Examiner*—Lyman H. Smith
*Attorney, Agent, or Firm*—Sughrue, Mion, Zinn, Macpeak & Seas, PLLC

[57] ABSTRACT

A process for producing perfluorocarbons which comprises a step of contacting a hydrofluorocarbon with fluorine gas in a vapor phase at an elevated reaction temperature in a first reaction zone to obtain a gaseous reaction mixture; and a step of introducing the gaseous reaction mixture as a diluent gas into a second reaction zone and contacting the same therein at an elevated reaction temperature with a hydrofluorocarbon fed to the second reaction zone if necessary together with fluorine gas, the hydrofluorocarbon fed to the second reaction zone being different from the hydrofluorocarbon reacted in the first reaction zone.

14 Claims, 1 Drawing Sheet

PROCESS FOR PRODUCING PERFLUOROCARBON

FIELD OF THE INVENTION

The present invention relates to a process for producing perfluorocarbons by reacting hydrofluorocarbons with fluorine gas in a vapor phase, and more particularly, a process for producing perfluorocarbons which comprises contacting a hydrofluorocarbon with fluorine gas in a vapor phase at an elevated reaction temperature in a first reaction zone, introducing the resulting gaseous reaction mixture as a diluent gas into a second reaction zone, and feeding a hydrofluorocarbon different from that reacted in the first reaction zone to the second reaction zone if necessary together with fluorine gas to contact the hydrofluorocarbon with the gaseous reaction mixture at an elevated reaction temperature. Perfluorocarbons which are gaseous at ordinary temperature are used, for example, as etchants and cleaning agents in the semiconductor industry, while perfluorocarbons which are liquid at ordinary temperature are used, for example, as refrigerants. Thus, perfluorocarbons have a wide range of applications and are industrially useful compounds.

BACKGROUND OF THE INVENTION

With respect to the production of perfluorocarbons, various methods have hitherto been proposed. For example, in the case of tetrafluoromethane (hereinafter referred to as "FC-14" or "$CF_4$") which is the perfluorocarbon with one carbon atom, examples of the prior art processes include a method comprising reacting chlorotrifluoromethane ($CClF_3$) with HF in the presence of a catalyst (JP-B-62-10211; the term "JP-B" as used herein means an "examined Japanese patent publication"); a method comprising reacting dichlorodifluoromethane ($CCl_2F_2$) with HF in the presence of a catalyst (JP-B-42-3004); a method comprising reacting carbon tetrachloride ($CCl_4$) with HF (JP-B-43-10601); a method comprising reacting trifluoromethane ($CHF_3$) with $F_2$ (GB-1116920 (1968)); a method comprising reacting carbon (C) with $F_2$ in $BrF_3$ or $IF_5$ (JP-A-58-162536; the term "JP-A" as used herein means an "unexamined published Japanese patent application"); and a method comprising pyrolyzing tetrafluoroethylene ($CF_2=CF_2$) and $CO_2$ at a high temperature (U.S. Pat. No. 4,365,102 (1982)).

In the case of hexafluoroethane (hereinafter referred to as "FC-116" or "$CF_3CF_3$"), which is the perfluorocarbon with two carbon atoms, examples of the known processes include an electrochemical fluorination method using ethane and/or ethylene as a starting material; a pyrolytic method in which tetrafluoroethylene or another starting material is pyrolyzed; a method comprising fluorinating acetylene, ethylene, and/or ethane, etc. with a metal fluoride; a method comprising fluorinating dichlorotetrafluoroethane, chloropentafluoroethane, or the like with hydrogen fluoride; and a direct fluorination method in which ethane or the like is reacted with fluorine gas.

Further, in the case of octafluoropropane (hereinafter referred to as "FC-218" or "$C_3F_8$"), which is the perfluorocarbon with three carbon atoms, examples of the known processes include a direct fluorination method in which fluorine gas is reacted with propane (EP-31,519 (1981)).

Examples of the direct fluorination method in which fluorine gas is used include (a) a method in which fluorine gas is reacted with ethane by means of a jet reactor to obtain FC-14 and FC-116 (*J. Amer. Chem. Soc.*, 77, 3307 (1955), *J. Amer. Chem. Soc.*, 82, 5827 (1960)); (b) a method in which C—H is fluorinated with fluorine gas by means of a reactor having a porous alumina pipe (EP-31,519 (1981)); and (c) a method in which a linear hydrocarbon is fluorinated with fluorine gas in the presence of a diluent gas by means of a reactor having a porous metal pipe (double-pipe reactor), the diluent gas being $SF_6$, $CF_4$, $C_2F_6$, or $C_3F_8$ (EP-32,210 (1981)).

Other known examples of the reaction using fluorine gas include (d) a method in which fluorine gas is reacted with a saturated or unsaturated hydrocarbon or a partially fluorinated hydrocarbon to produce a hydrofluorocarbon (U.S. Pat. NO. 5,406,008 (1995)); and a method in which a fluorinated alkene is produced from an alkene and carbon onto which fluorine gas has been adsorbed (JP-A-2-207052).

The direct fluorination method using fluorine gas has drawbacks that since fluorine gas, which is extremely reactive, is used, there is a danger of explosion of the organic compound as a substrate and fluorine gas and there is a danger of corrosion, etc. In addition, there are a danger of side reactions including the cleavage and polymerization of C—C bonds due to heat generation and a fear of an abrupt reaction or explosion due to the formation and deposition of carbon (C), etc.

For example, in the case of synthesizing a perfluorocarbon by the direct fluorination method in which a linear hydrocarbon compound is reacted with fluorine gas, the reaction is accompanied by an exceedingly large quantity of heat as shown in schemes (2) and (3).

(2)

($\Delta H = -479$ Kcal/mol)

(3)

($\Delta H = -690$ Kcal/mol)

The above schemes show that the replacement of one C—H bond by a C—F bond results in a heat of reaction of about $-110$ Kcal/mol. In the direct fluorination method in which propane is reacted with fluorine gas, $\Delta H$ is about $-880$ Kcal/mol.

The reaction shown by scheme (2), in which methane is used as a starting material, needs 4 mol of fluorine per mol of methane, while the reaction shown by scheme (3), in which ethane is used as a starting material, needs 6 mol of fluorine per mol of ethane. Thus, the quantity of heat of reaction is proportional to the number of moles of the fluorine used; the larger the fluorine amount, the larger the quantity of heat of reaction. The increased heat of reaction tends to cause the cleavage of C—C bonds, explosion, etc., and results in a reduced yield, thus posing problems concerning industrial production and operation. Conventional techniques used for inhibiting the abrupt generation of heat of reaction in the direct fluorination method include: to dilute fluorine with an inert gas (e.g., nitrogen or helium); to dissolve the organic compound as a substrate beforehand into a solvent inert to fluorine to prepare a low-concentration solution; and to conduct the reaction in a low-temperature region. For the reaction conducted in a vapor phase, a devised apparatus such as, e.g., a jet reactor has been proposed so that fluorine comes into contact with the organic compound as a substrate little by little.

SUMMARY OF THE INVENTION

The present invention has been achieved in order to eliminate the problems described above and to accomplish the subject described above. Accordingly, an object of the present invention is to provide a process by which perfluorocarbons can be safely and efficiently produced industrially at low cost by the direct fluorination method using organic compounds as substrates and fluorine gas.

Other objects and effects of the present invention will be apparent from the following description.

The present invention provides a process for producing perfluorocarbons which comprises a step of contacting a hydrofluorocarbon with fluorine gas in a vapor phase at an elevated reaction temperature in a first reaction zone to obtain a gaseous reaction mixture; and a step of introducing the gaseous reaction mixture as a diluent gas into a second reaction zone and contacting the same therein at an elevated reaction temperature with a hydrofluorocarbon fed to the second reaction zone if necessary together with fluorine gas, the hydrofluorocarbon fed to the second reaction zone being different from the hydrofluorocarbon reacted in the first reaction zone. In the present invention, at least part of the gaseous reaction mixture obtained in the second reaction zone is preferably circulated and used as a diluent gas for the first reaction zone.

DETAILED DESCRIPTION OF THE INVENTION

Figure 1:
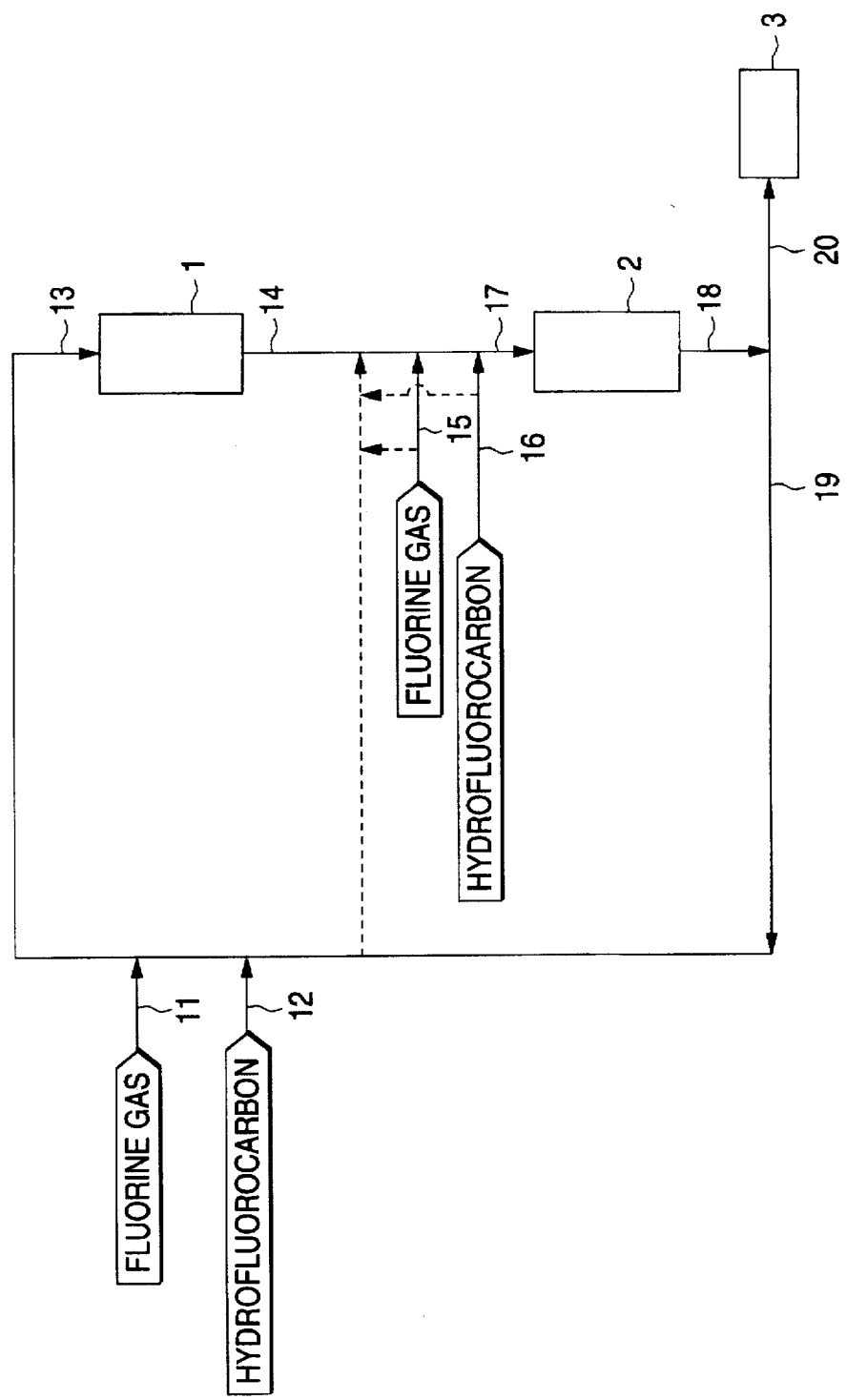
FIG. 1 shows a flow chart of an embodiment of the present invention.

Examples of usable diluent gases include tetrafluoromethane, hexafluoroethane, octafluoropropane, and hydrogen fluoride. Of these, tetrafluoromethane, hexafluoroethane, and hydrogen fluoride are preferred. A more preferred is a gas rich in hydrogen fluoride (the hydrogen fluoride content thereof being preferably 50% or higher based on the total amount of the diluent gas).

In carrying out the reactions, the hydrofluorocarbons used as starting materials are preferably introduced into the respective reaction zones so that the concentration of each hydrofluorocarbon as measured at the reaction zone inlet is 8 mol % or lower. The reactions are conducted at an elevated temperature; the first reaction zone and/or the second reaction zone desirably has a reaction temperature of from 200° to 550° C. Further, the first reaction zone and/or the second reaction zone desirably has a reaction pressure of from 0 to 5 MPa.

Two or more perfluorocarbons are obtained through the reactions. Examples thereof include FC-14, FC-116, and FC-218. Preferred are FC-14 and FC-116.

The hydrofluorocarbons fed as starting materials are two or more hydrofluorocarbons represented by the general formula $C_xH_yF_z$ (wherein x, y, and z are integers satisfying $1 \leq 3$, $1 \leq y \leq 4$, and $1 \leq z \leq 7$, provided that y+z=4 when x is 1, y+z=6 when x is 2, and y+z=8 when x is 3). The hydrofluorocarbons are desirably selected from the group consisting of fluoromethane ($CH_3F$), difluoromethane ($CH_2F_2$), trifluoromethane ($CHF_3$), trifluoroethane ($C_2H_3F_3$), tetrafluoroethane ($C_2H_2F_4$), pentafluoroethane ($C_2HF_5$), pentafluoropropane ($C_3H_3F_5$), hexafluoropropane ($C_3H_2F_6$), and heptafluoropropane ($C_3HF_7$). Preferred of these are fluoromethane, difluoromethane, trifluoromethane, trifluoroethane, tetrafluoroethane, and pentafluoroethane.

Especially preferred are difluoromethane, trifluoromethane, tetrafluoroethane, and pentafluoroethane.

The hydrofluorocarbons fed as starting materials preferably have a concentration of chlorine compound impurities of 2 mol % or lower.

The process for producing perfluorocarbons according to the present invention is explained below in detail.

The process of the present invention for producing perfluorocarbons comprises contacting a hydrofluorocarbon with fluorine gas in a vapor phase at an elevated reaction temperature in a first reaction zone, introducing the resulting gaseous reaction mixture (a perfluorocarbon and/or hydrogen fluoride) as a diluent gas into a second reaction zone, and feeding a hydrofluorocarbon different from that reacted in the first reaction zone to the second reaction zone if necessary together with fluorine gas to contact the hydrofluorocarbon with the gaseous reaction mixture at an elevated reaction temperature. At least part of the gaseous reaction mixture (a perfluorocarbon and/or hydrogen fluoride) obtained in the second reaction zone is preferably circulated and used as a diluent gas for the first reaction zone, whereby the problems of the conventional direct fluorination methods are eliminated and useful perfluorocarbons can be industrially produced safely and efficiently at low cost.

One of the features of the present invention resides in diluent gases.

In the case of the production of perfluorocarbons through the reactions of hydrofluorocarbons with fluorine gas, the reaction schemes and the heats of reaction are as shown below as schemes (4) to (7).

$$CH_2F_2 + 2F_2 \rightarrow CF_4 + 2HF \quad (4)$$

$$(\Delta H = -259 Kcal/mol)$$

$$CHF_3 + F_2 \rightarrow CF_4 + HF \quad (5)$$

$$(\Delta H = -120 Kcal/mol)$$

$$CF_3CH_2F + 2F_2 \rightarrow CF_3CF_3 + 2HF \quad (6)$$

$$(\Delta H = -231 Kcal/mol)$$

$$CF_3CHF_2 + F_2 \rightarrow CF_3CF_3 + HF \quad (7)$$

$$(\Delta H = -119 Kcal/mol)$$

Although an inert gas such as nitrogen, helium, or argon is generally employed as a diluent gas, this method is not always advantageous in cost in view of the necessity of the separation of the objective perfluorocarbons from these inert gases in the distillation step, purification, etc. An economically advantageously used diluent gas is a yielded gaseous reaction mixture which comprises tetrafluoromethane, hexafluoroethane, octafluoropropane, and hydrogen fluoride, desirably comprises tetrafluoromethane, hexafluoroethane, and hydrogen fluoride, and preferably rich in hydrogen fluoride.

In the present invention, hydrogen fluoride (boiling point: 20° C.) is yielded as a by-product as shown in, e.g., schemes (4) to (7). For example, in the case of using difluoromethane as a starting organic compound, 1 mol of FC-14 is yielded along with 2 mol of hydrogen fluoride. In the case of pentafluoroethane, 1 mol of FC-116 is yielded along with 1 mol of hydrogen fluoride. Since the difference in boiling point between the objective compound, i.e., FC-14 (boiling point: −127.9° C.) or FC-116 (boiling point: −78.5° C.), and the by-product, i.e., hydrogen fluoride, is about 100° C., the hydrogen fluoride can be easily separated through a distillation/purification step. Those compounds are also advantageous in energy cost for separation and purification because they have a higher boiling point than helium (boiling point: −286.9° C.) and other diluent gases.

Further, the use of the gaseous reaction mixture (a perfluorocarbon and hydrogen fluoride) without any treatment as a diluent gas is advantageous in cost. Although hydrogen fluoride may be recovered in a distillation/purification step and circulated for use as a diluent gas, the recovered hydrogen fluoride is usually used in other applications. In the direct fluorination method in which fluorine gas is used, carbon formation, deposition, etc. occur as a result of C—C bond cleavage, polymerization, etc. during the long-term reaction as stated hereinabove. Although the carbon formation, deposition, etc. may cause a ganger of an abrupt reaction with fluorine gas or explosion, the use of a diluent gas rich in hydrogen fluoride is effective in inhibiting the formation and deposition of carbon. The term "rich in hydrogen fluoride" means "containing hydrogen fluoride as a major component."

The reactions of hydrofluorocarbons (reaction substrates) with fluorine gas are conducted in the presence of a diluent gas. Before being introduced into a reactor, either or both of the reaction substrates and fluorine gas are generally diluted with the diluent gas. From the standpoint of safety, both the reaction substrates and the fluorine gas are desirably diluted with the diluent gas in a sufficiently low concentration.

In the present invention, the reactions are preferably conducted while regulating the concentration of each hydrofluorocarbon reaction substrate as measured at the reactor inlet to 8 mol % or lower. As stated hereinabove, in the direct fluorination method in which fluorine gas is used, there is the danger that the organic compound as a substrate (in particular a compound containing hydrogen) may burn or explode upon exposure to fluorine, because fluorine is extremely reactive. In the reactions of the present invention, it is important that since hydrofluorocarbons, containing hydrogen, are used as the organic compound substrates, the explosion of the hydrofluorocarbons and fluorine should be prevented. For preventing explosion, the mixed gases should be regulated so as to have a composition outside the explosion range therefor. As a result of investigations made by the present inventors on the explosion ranges for mixtures of hydrofluorocarbons with fluorine gas, it was found that the lower limits of the explosion ranges for these hydrofluorocarbons were 8 mol % or lower, although they vary depending on the kinds of the hydrofluorocarbons. Based on this, the safety ranges of the inlet concentrations of the organic compounds in the reactions can be determined.

Reaction temperature is among the conditions which should be taken in account in order to efficiently carry out the reactions. The optimum range of reaction temperature varies depending on the contact time and the kinds of the hydrofluorocarbons as starting materials. For example, in the case where the reaction of 1,1,1,2-tetrafluoroethane with fluorine is conducted in the presence of a diluent gas using a long contact time (15 seconds), the reaction begins at a reaction temperature of about 50° C. and the conversion reaches about 100% at a temperature of about 250° C. An elevated reaction temperature is used, preferably in the range of from 200° to 550° C. for each of the first reaction zone and the second reaction zone.

Reaction temperatures lower than 200° C. are not preferred in that the conversions of the hydrofluorocarbons are low. Reaction temperatures exceeding 550° C. are undesirable in, for example, that C—C bond cleavage, polymerization, etc. occur to result in a reduced yield, and that there are problems such as reactor corrosion and an increased energy cost. Although the contact time is not particularly limited, it is in the range of, for example, from 0.1 to 120 seconds. In general, however, the contact time is desirably from 1 to 30 seconds, preferably from 3 to 30 seconds, since longer contact times necessitate a larger reactor and are hence uneconomical. It is preferred to well mix the reaction substrates with the fluorine gas.

The molar ratio of the fluorine gas to the hydrofluorocarbon both fed to each reaction system is preferably from 0.5 to 5.0, more preferably from 1.0 to 3.0. If the molar proportion of the fluorine gas fed is below 0.5, the reaction does not proceed efficiently. Molar proportions thereof exceeding 5.0 are uneconomical in that fluorine gas is fed in excess and this necessitates, for example, an apparatus for the recovery thereof. Methods for feeding fluorine gas are not particularly limited. For example, use may be made of a method in which fluorine gas is fed in excess to the first reaction zone and the fluorine gas remaining unreacted is used for the reaction in the second reaction zone. In general, however, it is preferred from the standpoint of safety to feed fluorine gas to both of the first reaction zone and the second reaction zone.

In carrying out the reactions, the reaction pressure is also important from the standpoint of preventing dangers such as explosion. In general, the higher the pressure, the wider the explosion range. Consequently, the reactions are conducted desirably at a lower pressure. Specifically, the reaction pressure for both of the first reaction zone and the second reaction zone is in the range of desirably from 0 to 5 MPa, preferably from 0 to 3 MPa.

The reactor is preferably made of a material having resistance to corrosive gases. Examples of the material include nickel, Inconel, and Hastelloy.

As stated hereinabove, the direct fluorination method in which an organic compound as a substrate is reacted with fluorine gas is accompanied by an exceedingly large quantity of heat, and the quantity of heat of reaction is proportional to the number of moles of the fluorine gas used, i.e., the larger the fluorine amount, the larger the quantity of heat of reaction. Because of this, the smaller the number of C—H bonds which should be replaced by C—F bonds, the easier the control of the heat of reaction and the smaller the use amount of fluorine, which is expensive, i.e., the lower the cost.

Another feature of the present invention resides in substrates. As stated hereinabove, the organic compounds used as substrates in the present invention are not linear hydrocarbons containing a larger number of C—H bonds which should be replaced by C—F bonds, but hydrofluorocarbons (HFC), which have been partially fluorinated. Due to the use of such substrates, in which the number of C—H bonds which should be replaced by C—F bonds is small, the control of the heat of reaction is easy. Two or more hydrofluorocarbons are fed in this invention to produce two or more perfluorocarbons. Examples of usable hydrofluorocarbons are represented by formula (8):

$$C_xH_yF_z \tag{8}$$

(wherein x, y, and z are integers satisfying $1 \leq x \leq 3$, $1 \leq y \leq 4$, and $1 \leq z \leq 7$, provided that y+z=4 when x is 1, y+z=6 when x is 2, and y+z=8 when x is 3).

The substrates are desirably selected from hydrofluorocarbons containing up to three C—H bonds which should be replaced by C—F bonds, specifically, fluoromethane, difluoromethane, trifluoromethane, trifluoroethane, tetrafluoroethane, pentafluoroethane, pentafluoropropane, hexafluoropropane, and heptafluoropropane. Preferred of these from the standpoint of availability, etc. are fluoromethane, difluoromethane, trifluoromethane, trifluoroethane, tetrafluoroethane, and pentafluoroethane. Especially preferred are hydrofluorocarbons containing up to two C—H bonds which should be replaced by C—F bonds, specifically, difluoromethane, trifluoromethane, trifluoroethane, tetrafluoroethane, and pentafluoroethane. These hydrofluorocarbons are being industrially produced, for example, as substitutes for chlorofluorocarbons (CFC) or hydrochlorofluorocarbons (HCFC) and as refrigerants. Such commercial products have a purity of 99.9% or higher, which is satisfactory.

Thus, the use of hydrofluorocarbons such as those enumerated above has an advantage that the quantity of heat of reaction can be as small as about from ½ to ⅙ (schemes (4) to (7)) of those in the production of perfluorocarbons from linear hydrocarbon compounds and fluorine gas (schemes (2) and (3)).

Those hydrofluorocarbons may be used either alone or as a mixture thereof. From the hydrofluorocarbons, two or more perfluorocarbons are obtained as the objective compounds. Preferred perfluorocarbons are tetrafluoromethane, hexafluoroethane and/or octafluoropropane, and more preferred are tetrafluoromethane and hexafluoroethane.

The hydrofluorocarbons used as starting materials for the reactions desirably contain no chlorine compounds. Inclusion of chlorine compounds is undesirable from the standpoints of reactor material and distillation operation because they undergo reactions to yield chlorine and chlorine fluoride. The concentration of chlorine compounds in each hydrofluorocarbon is desirably 2 mol % or lower, preferably 1 mol % or lower, especially preferably 0.1 mol % or lower.

Still another feature of the present invention resides in that a process further improved in cost, safety, and efficiency is provided due to the features described above. This process comprises contacting a hydrofluorocarbon with a fluorine gas in a vapor phase at an elevated reaction temperature in a first reaction zone to yield a first perfluorocarbon and hydrogen fluoride; introducing part or all of these as a diluent gas into a second reaction zone; feeding to the second reaction zone a hydrofluorocarbon different from that fed to the first reaction zone if necessary together with fluorine gas to contact the hydrofluorocarbon with the diluent gas at an elevated reaction temperature and to thereby yield a second perfluorocarbon and hydrogen fluoride; and circulating part or all of these to the first reaction zone and/or the second reaction zone to use the same as a diluent gas.

For example, 1,1,1,2-tetrafluoroethane as a hydrofluorocarbon and fluorine gas are fed to a first reaction zone having an elevated temperature together with a gas rich in hydrogen fluoride as a diluent gas to yield FC-116 as a perfluorocarbon and hydrogen fluoride in the first reaction zone in a vapor phase. Part of the reactor outlet gas may be used as it is as a diluent gas, or the outlet gas may be sent to a distillation step. However, the outlet gas is usually introduced into a second reactor. At the inlet of the second reactor, a different kind of hydrofluorocarbon, e.g., difluoromethane, is mixed with the outlet gas discharged from the first reaction zone, if necessary together with fluorine gas. The mixture is fed to the second reactor having an elevated reaction temperature to yield FC-14 as a perfluorocarbon and hydrogen fluoride.

The outlet gas discharged from the second reaction zone is a mixture comprising FC-116 and FC-14, as perfluorocarbons, and hydrogen fluoride generated as a by-product in a larger amount than the perfluorocarbons. Part of this mixture obtained as an outlet gas discharged from the second reaction zone is circulated to the first reaction zone and/or the second reaction zone and used as it is as a diluent gas. The remainder is separated into the perfluorocarbons and hydrogen fluoride in distillation and purification steps.

Compared to the ordinary processes in which one perfluorocarbon is produced from one hydrofluorocarbon, the process of the present invention, in which two or more perfluorocarbons are produced from two or more hydrofluorocarbons as described above, is advantageous in, for example, that the equipment for a distillation step can be simplified and a reduced energy cost is attained.

Although reaction zones may be formed by partitioning one reactor, it is usually preferred to use two or more reactors from the standpoints of easiness of operation and safety. Reactors may be arranged either in a row or in series, but are usually preferably arranged in series.

It is possible to produce one perfluoro compound, e.g., FC-14, from two or more hydrofluorocarbons, e.g., difluoromethane and trifluoromethane. It is also possible to feed one hydrofluorocarbon, e.g., difluoromethane, to both of the first reaction zone and the second reaction zone to conduct the reaction mildly.

In the present invention, the proportions of two hydrofluorocarbons fed as starting materials may be changed to change the proportions of the two perfluorocarbons to be yielded therefrom. It is also possible to use three or more reaction zones to simultaneously yield three or more perfluorocarbons.

As described above, according to the process of the present invention, perfluorocarbons can be industrially produced safely and efficiently at low cost.

The following are Examples of the present invention, but the invention should not be construed as being limited thereto.

The hydrofluorocarbons used as starting materials in the following reactions are shown below first.

(Difluoromethane)

Difluoromethane ($CH_2F_2$) Ecoloace 32 (trade name, manufactured by Showa Denko K. K., Japan), which is currently being supplied as a substitute for HCFC-22 (CHClF2), was used.

It had a purity of 99.99% or higher, and contained 1,1,1-trifluoroethane ($CF_3CH_3$) and fluoromethane ($CH_3F$) as impurities. Almost no chlorine compound was detected therein.

(Trifluoromethane)

Trifluoromethane ($CHF_3$) Ecoloace 23 (trade name, manufactured by Showa Denko K. K.), which is currently being supplied as a refrigerant, was used. It had a purity of 99.95% or higher, and contained chlorine compounds including chlorodifluoromethane ($CHClF_2$) and chlorotrifluoromethane ($CClF_3$) as impurities.

(1,1,1,2-Tetrafluoroethane)

1,1,1,2-Tetrafluoroethane ($CF_3CH_2F$) Ecoloace 134a (trade name, manufactured by Showa Denko K. K.), which is currently being supplied as a substitute for CFC-12 ($CClF_2$), was used. It had a purity of 99.99% or higher, and contained 1,1,2,2-tetrafluoroethane, an isomer. No chlorine compound was detected therein.

(Pentafluoroethane)

Pentafluoroethane ($CF_3CHF_2$) Ecoloace 125 (trade name, manufactured by Showa Denko K. K.), which is currently being supplied as a substitute for HCFC-22 ($CHClF_2$), was used. It had a purity of 99.95% or higher, and contained, as impurities, $CF_3CH_2F$, $CF_3CH_3$, and chlorine compounds, i.e., chloropentafluoroethane ($CF_3CClF_2$) and 1-chloro-1,2,2,2-tetrafluoroethane ($CHClFCF_3$).

EXAMPLE 1

FIG. 1 is a flow chart of one embodiment of the perfluorocarbon production process of the present invention. The trifluoromethane described above was mixed as a hydrofluorocarbon (12) with fluorine gas (11) and a diluent gas (19), and the mixed gas (13) was introduced into a first reaction zone (1). In the first reaction zone, the reactants were reacted under the conditions of a reaction pressure of 1.5 MPa, a reaction temperature of 400° C., an $F_2$/trifluoromethane molar ratio of 1.51, and an inlet concentration of trifluoromethane of 2.1 mol %. Thus, an outlet gas (14) discharged from the first reaction zone was obtained.

With this outlet gas were mixed 1,1,1,2-tetrafluoroethane as a fresh hydrofluorocarbon (16) and fluorine gas (15). This mixed gas (17) was introduced into a second reaction zone (2). In the second reaction zone, the reactants were reacted under the conditions of a reaction pressure of 1.5 MPa, a reaction temperature of 370° C., an $F_2$/1,1,1,2-tetrafluoroethane molar ratio of 2.06, and an inlet concentration of 1,1,1,2-tetrafluoroethane of 1.35 mol %. Thus, an outlet gas (18) discharged from the second reaction zone was obtained. This outlet gas was divided into a diluent gas (19) and a gas (20) to be introduced into a distillation/purification step (3). The results obtained are shown in Table 1, wherein the numerals given in the uppermost section correspond to the numerals given in FIG. 1.

EXAMPLE 2

Perfluorocarbons were produced by a process shown by the same flow chart as in Example 1, as follows. Pentafluoroethane was mixed as a hydrofluorocarbon (12) with fluorine gas (11) and a diluent gas (19), and the mixed gas (13) was introduced into a first reaction zone (1). In the first reaction zone, the reactants were reacted under the conditions of a reaction pressure of 1.5 MPa, a reaction temperature of 370° C., an $F_2$/pentafluoroethane molar ratio of 1.47, and an inlet concentration of pentafluoroethane of 3.2 mol %. Thus, an outlet gas (14) discharged from the first reaction zone was obtained.

With this outlet gas were mixed difluoromethane as a fresh hydrofluorocarbon (16) and fluorine gas (15). This mixed gas (17) was introduced into a second reaction zone (2). In the second reaction zone, the reactants were reacted under the conditions of a reaction pressure of 1.5 MPa, a reaction temperature of 350° C., an $F_2$/difluoromethane molar ratio of 2.01, and an inlet concentration of difluoromethane of, 2.05 mol %. Thus, an outlet gas (18) discharged from the second reaction zone was obtained. This outlet gas was divided into a diluent gas (19) and a gas (20) to be introduced into a distillation/purification step. The results obtained are shown in Table 2.

TABLE 1

(Example 1)

| Component | 11 | 12 | 13 | 14 | 15 | 16 | 17 | 18 | 19 | 20 |
|---|---|---|---|---|---|---|---|---|---|---|
| $F_2$ | 1.003 | — | 1.012 | 0.367 | 0.585 | — | 0.952 | 0.010 | 0.009 | 0.001 |
| HFC-134a | — | — | 0.004 | — | — | 0.462 | 0.462 | 0.004 | 0.004 | — |
| HFC-23 | — | 0.665 | 0.668 | 0.047 | — | — | 0.047 | 0.003 | 0.003 | — |
| HF | — | — | 17.288 | 17.933 | — | — | 17.933 | 18.873 | 17.288 | 1.585 |
| HFC-125 | — | — | 0.030 | 0.015 | — | — | 0.015 | 0.033 | 0.030 | 0.003 |
| FC-116 | — | — | 4.983 | 5.002 | — | — | 5.002 | 5.440 | 4.983 | 0.457 |
| FC-14 | — | — | 7.295 | 7.916 | — | — | 7.916 | 7.964 | 7.295 | 0.669 |
| Others | 0.010 | 0.001 | 0.031 | 0.031 | 0.007 | — | 0.038 | 0.038 | 0.020 | 0.018 |
| Total | 1.013 | 0.666 | 31.489 | 31.489 | 0.592 | 0.462 | 32.365 | 32.365 | 29.632 | 2.733 |

The unit of the amount of each component in the table is Kmol/hr. In the table, HFC-134a is 1,1,1,2-tetrafluoroethane, HFC-23 is trifluoromethane, and HFC-125 is pentafluoroethane.

TABLE 2

(Example 2)

| Component | 11 | 12 | 13 | 14 | 15 | 16 | 17 | 18 | 19 | 20 |
|---|---|---|---|---|---|---|---|---|---|---|
| $F_2$ | 1.505 | — | 1.514 | 0.516 | 0.878 | — | 0.394 | 0.015 | 0.009 | 0.006 |
| HFC-125 | — | 0.9980 | 1.028 | 0.045 | — | — | 0.045 | 0.034 | 0.030 | 0.004 |
| HFC-32 | — | — | — | — | — | 0.693 | 0.693 | — | — | — |
| HF | — | — | 17.288 | 18.286 | — | — | 18.286 | 19.665 | 17.288 | 2.377 |
| HFC-23 | — | — | 0.030 | 0.015 | — | — | 0.015 | 0.033 | 0.030 | 0.003 |
| FC-116 | — | — | 4.983 | 5.966 | — | — | 5.966 | 5.977 | 4.983 | 0.994 |
| FC-14 | — | — | 7.295 | 7.310 | — | — | 7.310 | 7.985 | 7.295 | 0.690 |
| Others | 0.014 | 0.002 | 0.036 | 0.036 | 0.007 | — | 0.043 | 0.043 | 0.020 | 0.023 |
| Total | 1.519 | 1.000 | 32.174 | 32.174 | 0.885 | 0.693 | 33.752 | 33.752 | 29.655 | 4.097 |

The unit of the amount of each component in the table is Kmol/hr. In the table, HFC-125 is pentafluoroethane, HFC-32 is difluoromethane, and HFC-23 is trifluoromethane.

According to the present invention, a process can be provided by which perfluorocarbons are industrially produced safely and efficiently at low cost.

While the invention has been described in detail and with reference to specific embodiments thereof, it will be apparent to one skilled in the art that various changes and modifications can be made therein without departing from the spirit and scope thereof.

We claim:

1. A process for producing perfluorocarbons which comprises a step of contacting a hydrofluorocarbon with fluorine gas in a vapor phase at an elevated reaction temperature in a first reaction zone to obtain a gaseous reaction mixture; and a step of introducing the gaseous reaction mixture as a diluent gas into a second reaction zone and contacting the same therein at an elevated reaction temperature with a hydrofluorocarbon fed to the second reaction zone if necessary together with fluorine gas, the hydrofluorocarbon fed to the second reaction zone being different from the hydrofluorocarbon reacted in the first reaction zone.

2. The process as claimed in claim 1, wherein at least part of the gaseous reaction mixture obtained in the second reaction zone is used as a diluent gas for the first reaction zone.

3. The process as claimed in claim 1, wherein the diluent gas for the first reaction zone and/or the second reaction zone contains at least one of tetrafluoromethane, hexafluoroethane, octafluoropropane, and hydrogen fluoride.

4. The process as claimed in claim 1, wherein the diluent gas is rich in hydrogen fluoride.

5. The process as claimed in claim 1, wherein the concentration of the hydrofluorocarbon as measured at the inlet to the first reaction zone and/or the second reaction zone is 8 mol % or lower.

6. The process as claimed in claim 1, wherein the first reaction zone and/or the second reaction zone has a reaction temperature of from 200° to 550° C.

7. The process as claimed in claim 1, wherein the first reaction zone and/or the second reaction zone has a reaction pressure of from 0 to 5 MPa.

8. The process as claimed in claim 1, wherein the perfluorocarbons yielded is two or more kinds.

9. The process as claimed in claim 8, wherein the perfluorocarbons yielded are at least two members selected from tetrafluoromethane, hexafluoroethane, and octafluoropropane.

10. The process as claimed in claim 9, wherein the perfluorocarbons yielded are tetrafluoromethane and hexafluoroethane.

11. The process as claimed in claim 1, wherein the hydrofluorocarbons are represented by formula (1)

$$C_xH_yF_z \qquad (1)$$

wherein x, y, and z are integers satisfying $1 \leq x \leq 3$, $1 \leq y \leq 4$, and $1 \leq z \leq 7$, provided that y+z=4 when x is 1, y+z=6 when x is 2, and y+z=8 when x is 3.

12. The process as claimed in claim 11, wherein the hydrofluorocarbons are at least two members selected from the group consisting of fluoromethane, difluoromethane, trifluoromethane, trifluoroethane, tetrafluoroethane, pentafluoroethane, pentafluoropropane, hexafluoropropane, and heptafluoropropane.

13. The process as claimed in claim 12, wherein the hydrofluorocarbons are at least two members selected from difluoromethane, trifluoromethane, tetrafluoroethane, and pentafluoroethane.

14. The process as claimed in claim 11, wherein the hydrofluorocarbons used have a concentration of chlorine compound impurities of 2 mol % or lower.

* * * * *